United States Patent [19]

Grabenkort

[11] Patent Number: 5,427,145
[45] Date of Patent: Jun. 27, 1995

[54] CONNECTOR WITH INTEGRAL VALVE

[75] Inventor: Richard W. Grabenkort, Barrington, Ill.

[73] Assignee: Abbott Laboratories, Abbott Park, Ill.

[21] Appl. No.: 133,688

[22] Filed: Oct. 7, 1993

[51] Int. Cl.⁶ .................. F16K 5/04; F16K 11/085
[52] U.S. Cl. .................. 137/616.7; 137/625.23; 137/625.47; 128/203.12; 604/283; 604/905
[58] Field of Search ......... 137/616.7, 625.23, 625.47; 604/283, 905; 128/203.12, 203.25, 203.14, 203.24

[56] References Cited

U.S. PATENT DOCUMENTS 4,589,445  5/1986  Aguilar et al. ............ 137/616.7
5,144,984  9/1992  Westerberg et al. ....... 137/616.7 X

FOREIGN PATENT DOCUMENTS

249699  5/1948  Switzerland ............ 137/616.7

Primary Examiner—Arnold Rosenthal
Attorney, Agent, or Firm—Tom Breininger; Harry G. Thibault

[57] ABSTRACT

A connector is provided for mounting on an anesthetic vaporizer to connect the inlet of the vaporizer with a discharge port of a container of liquid anesthetic. The connector includes a first coupling attachable to the vaporizer and defining a first passage communicating at one end with the vaporizer inlet. A second coupling is attachable to the container and defines a second passage communicating at one end with the container discharge port. A third passage defined by one of the couplings and communicates with one of the first and second passages. A combination valve and mounting structure is cooperatively defined by the couplings to accommodate pivoting of the second coupling to a closed position occluding the first and second passages, to a raised fill position establishing communication between the first and second passages, and to a lowered drain position in which the first and second passages communicate through the third passage.

12 Claims, 4 Drawing Sheets

CONNECTOR WITH INTEGRAL VALVE

TECHNICAL FIELD

The present invention relates to a connector for connecting a container to a device into which liquid contents of the container are to be transferred. The connector is particularly well-suited for use in operating rooms to safely transfer an anesthetic from a container to a vaporizer while minimizing the likelihood of the anesthetic escaping to the atmosphere.

BACKGROUND OF THE INVENTION AND TECHNICAL PROBLEMS POSED BY THE PRIOR ART

Inhalable anesthetics are typically volatile substances with relatively low boiling points and high vapor pressures. They can be flammable and explosive substances in both their liquid and vapor states. Further, inhalation of the vapor by health care personnel using them can cause drowsiness.

Therefore, such anesthetics must be safely handled in operating rooms in order to minimize the risk of inhalation by medical personnel as well as to minimize the risk of fire or explosion. Preferably, the anesthetic should be used in a way which will ensure that there is little or no release to the atmosphere at all stages of handling during normal surgical procedures.

Anesthetics are typically dispensed in liquid form to an apparatus, such as an anesthetic vaporizer, which mixes the anesthetic with oxygen and nitrous oxide. The mixture is supplied in gaseous form to the patient for inhalation.

Devices have been designed for the transfer of an anesthetic from a supply container to a vaporizer through a closed system that eliminates the escape of an anesthetic gas to the atmosphere. The devices are designed so that during set-up and disassembly procedures, a supply container of anesthetic is not open and exposed to the atmosphere in the operating room.

One system which has been developed for connecting an anesthetic container to a vaporizer employs a connector tube having adaptors at both ends. The tube is flexible and is kink-resistant. The vaporizer end of the tube is provided with a vaporizer adaptor that engages an anesthetic vaporizer. The end of the tube attached to the anesthetic container is provided with a closure adaptor that engages a closure on the anesthetic container.

The closure is preferably connected to the supply container prior to use in the operating room. The container closure has a frangible seal adapted to be perforated by a piercing means within the closure adaptor as the adaptor engages the closure. Following perforation of the frangible seal by the piercing means, the closure adaptor and closure remain locked together, and this permits the transport of anesthetic through the tube from the supply container to the vaporizer. The system remains closed to the atmosphere throughout the assembly or disassembly procedures.

Further, some types of vaporizers are intended for use with only a specific anesthetic or anesthetics. In such situations, care must be taken to insure that only the proper anesthetic is dispensed into the particular vaporizer. Connecting devices have been designed with keying systems to prevent the use of a vaporizer with an anesthetic for which it is not designed.

In particular, the anesthetic container closure has a specific shape, and the connector tube closure adaptor has a complementary shape for mating with the container closure. At the other end of the container tube, the adaptor has a special shape for mating with a complementary portion of the vaporizer anesthetic inlet port. Because the container for each type of anesthetic has its own special closure shape, and because the corresponding connector device fits only the type of vaporizer designed for that anesthetic, the probability of inadvertently using an anesthetic in an incompatible vaporizer, or of administering an incorrect anesthetic to a patient, is greatly reduced, if not eliminated.

Although such keyed, connector tubes function satisfactorily, there are inventory, installation, and management considerations associated with their use. In particular, such connector tubes are typically provided to the user initially unattached to the vaporizer or the anesthetic container. Thus, such connector tubes must be stored and maintained at an appropriate location for use, and such connector tubes can become misplaced.

Because such connector tubes are not inexpensive, it would be desirable to provide an improved connector device that is less likely to be misplaced. Further, it would be advantageous to provide an improved system which is less expensive and even easier to use.

The above-described flexible tube connector must be held and properly manipulated as the anesthetic container is attached. Further, once attached, the container must be properly inverted and maintained in a generally inverted position so as to permit the anesthetic liquid to flow into the vaporizer. During this process, the flexible tube connector must be maintained at an elevation which is at or above the vaporizer inlet, and the connector must be maintained in an orientation that does not occlude the internal flow path.

Further, after the anesthetic liquid has drained from the container into the vaporizer, care must be taken in removing the container from the connector. Proper procedures must be followed to minimize the likelihood that a significant amount of residual anesthetic liquid in the container or flexible tube connector will drip or leak out as the container is disconnected.

It would be desirable to provide an improved connector which can be readily placed in a receiving orientation wherein the anesthetic container can be easily attached to the connector. Preferably, in this orientation the connector should function in a self-maintained, closed condition wherein the connector occludes flow of the liquid anesthetic out of the vaporizer and wherein the connector also occludes the connected container to prevent escape of the anesthetic liquid or vapor.

Further, it would be advantageous if such an improved connector could readily accommodate repositioning to a self-maintained orientation for accommodating the emptying of the anesthetic container into the vaporizer while the container is in a generally inverted position.

Additionally, such an improved connector should desirably accommodate removal of the empty anesthetic container. To this end, the improved connector should preferably have a self-maintained draining position to accommodate the draining of any residual anesthetic liquid in the top of the container and/or connector into the bottom of the container prior to removal of the container.

The present invention provides an improved connector which can accommodate designs having the above discussed benefits and features.

SUMMARY OF THE INVENTION

A connector suitable for attaching to or mounting on an anesthetic vaporizer is provided for connecting the inlet of the vaporizer with a discharge port of a container of liquid anesthetic.

In a preferred form, the connector has a stationary coupling that is attachable, preferably permanently, to the vaporizer. The connector also has a movable coupling that is pivotally mounted to the stationary coupling. The container discharge port is connected to the movable coupling for emptying the liquid contents through a single dispensing passage defined therein.

The stationary coupling includes an internal liquid passage system having the configuration of a "Y" oriented to lie on its side with one diverging branch slanting upwardly and with one diverging branch slanting downwardly. The horizontal stem of the Y-shaped passage communicates with the vaporizer. The two branches of the "sideways" Y-shaped passage system each extend to the movable coupling.

The movable coupling can be pivoted on the stationary coupling so that the container is inverted and so that the dispensing passage in the movable coupling slants upwardly and is aligned with the end of the upwardly slanting branch of the sideways Y-shaped passage. The liquid can then drain from the container through the slanting dispensing passage of the movable coupling, through the aligned branch and stem of the Y-shaped passage in the stationary coupling, and then into the vaporizer.

After all of the container liquid has emptied into the vaporizer, the movable coupling can be pivoted downwardly on the stationary coupling so as to align the movable coupling passage with the downwardly slanting, other branch of the Y-shaped passage. In this position, the movable coupling and attached container slant downwardly from the stationary coupling. This permits any residual liquid in the passages and in the top of the container to drain to the bottom of the container before the container is disconnected.

Prior to disconnecting the container, the movable coupling can be pivoted further downwardly to move the dispensing passage away from the lower branch of the Y-shaped passage in the stationary coupling. The mating, pivot surface of the movable coupling then functions as a valve member and blocks the openings to the two branches of the Y-shaped passage. This prevents fluid from flowing into or out of the stationary coupling attached to the vaporizer.

In the preferred form, an analogous set of passages is provided for venting air into the container to facilitate the draining of the liquid from the container.

The diverging passages of the invention need not define the specific Y-shaped passage system described above. Further, the diverging passage system could be provided in the movable coupling rather than in the stationary coupling.

Indeed, the invention can be more generally described with reference to first and second couplings having appropriate passage configurations. In particular, the first coupling can be characterized as being attachable to the vaporizer and defining a first through passage communicating at one end with the vaporizer inlet. The second coupling can be characterized as being attachable to the container and defining a second through passage communicating at one end with the container discharge port.

Either the first or second coupling can also be characterized as defining a third passage which communicates at one end with either the first or second passage.

A combination valve and mounting structure is cooperatively defined by the couplings to accommodate pivoting of the second coupling relative to the first coupling. The second coupling can be pivoted to a "closed" position occluding the first, second, and third passages.

The second coupling can also be pivoted to a raised, "fill" position establishing communication between the first and second passages whereby the anesthetic liquid can flow from the container into the vaporizer.

Finally, the second coupling can also be pivoted to a lowered, "drain" position in which the second coupling second passage slants downwardly. In the drain position, the third passage establishes communication between the first coupling first passage and the second coupling second passage.

Before lowering the second coupling to the drain position, the vaporizer inlet can be closed by a suitable valve on the vaporizer. Then, when the second coupling is moved to the drain position, any residual anesthetic liquid in the connector and/or the discharge port region on the container is permitted to drain under the influence of gravity back into the container prior to the container being disconnected from the connector.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same.

DESCRIPTION OF THE PREFERRED EMBODIMENTS

The present invention provides a novel system for connecting an anesthetic container to a vaporizer. The system includes a connector which can, if desired, be permanently affixed to the vaporizer and which includes safety features so that the vaporizer can be connected only to a container of the type of anesthetic for which the vaporizer has been designed.

The connector is relatively inexpensive and easy to use. Connecting an anesthetic container to the vaporizer with this device results in the liquid anesthetic draining directly to the vaporizer in a closed system that eliminates the escape of anesthetic to the atmosphere. Further, the connector, in its preferred form, has a plurality of self-maintained orientations. In one orientation the connector closes off the inlet to the vaporizer while a container full of anesthetic liquid is attached to the connector. In the closed position, the discharge port of the anesthetic container is occluded to prevent leakage or flow of the anesthetic liquid or gas.

The connector also has a fill position in which the container is generally inverted, and the connector permits the liquid anesthetic to drain from the container into the vaporizer.

Finally, the connector has a drain position in which the empty container is lower than the vaporizer fill port so that any residual anesthetic liquid in the connector and/or the container discharge region can flow back into the container before the container is removed from the connector. At this point, if desired, the vaporizer can be drained into the empty container.

While this invention is susceptible of embodiment in many different forms, this specification and the accompanying drawings disclose only some specific forms as examples of the invention. The invention is not intended to be limited to the embodiments so described, however. The scope of the invention is pointed out in the appended claims.

For ease of description, the system components of this invention are described in the normal operating position, and terms such as upper, lower, horizontal, etc., are used with reference to this position. It will be understood, however, that the components of this invention may be manufactured, stored, transported, and sold in an orientation other than the position described.

Figures illustrating the components of the invention show some mechanical elements that are known and that will be recognized by one skilled in the art. The detailed descriptions of such elements are not necessary to an understanding of the invention, and accordingly, are herein presented only to the degree necessary to facilitate an understanding of the novel features of the present invention.

Figure 1:
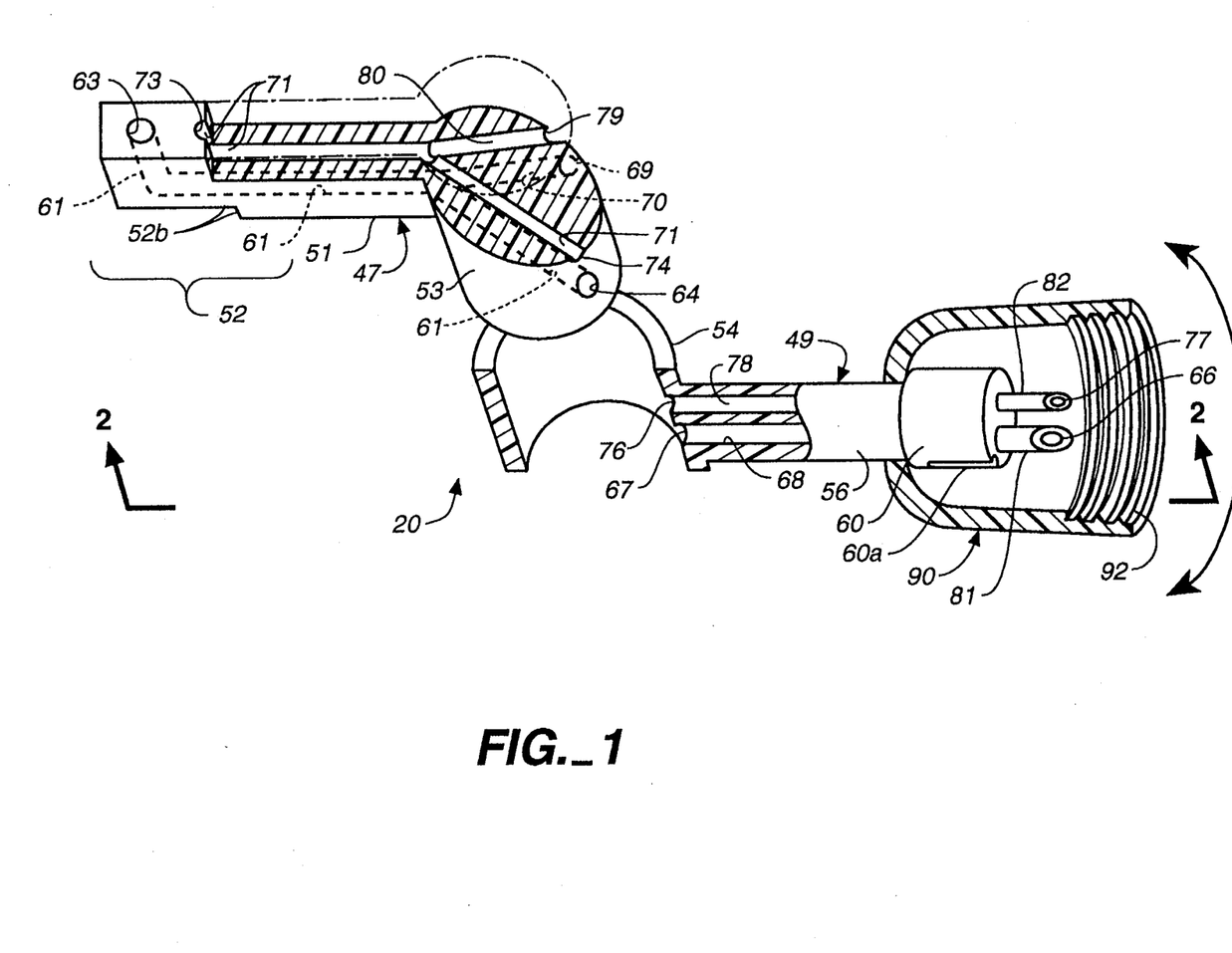
FIG. 1 is an exploded, perspective view of a connector of the present invention with portions of the structure broken away to illustrate interior detail.
Figure 4:
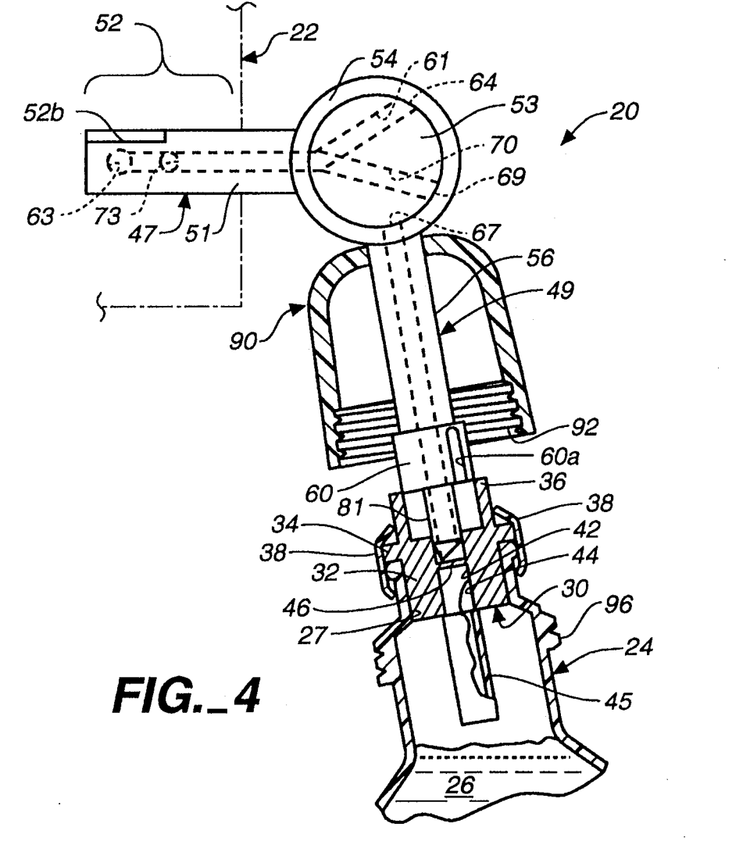
FIG. 4 is a fragmentary, partial, cross-sectional view similar to FIG. 2, but FIG. 4 shows the connector first coupling connected with an anesthetic vaporizer and shows the connector second coupling pivoted to a downwardly angled, closed position and partially engaged with a container.
Figure 5:
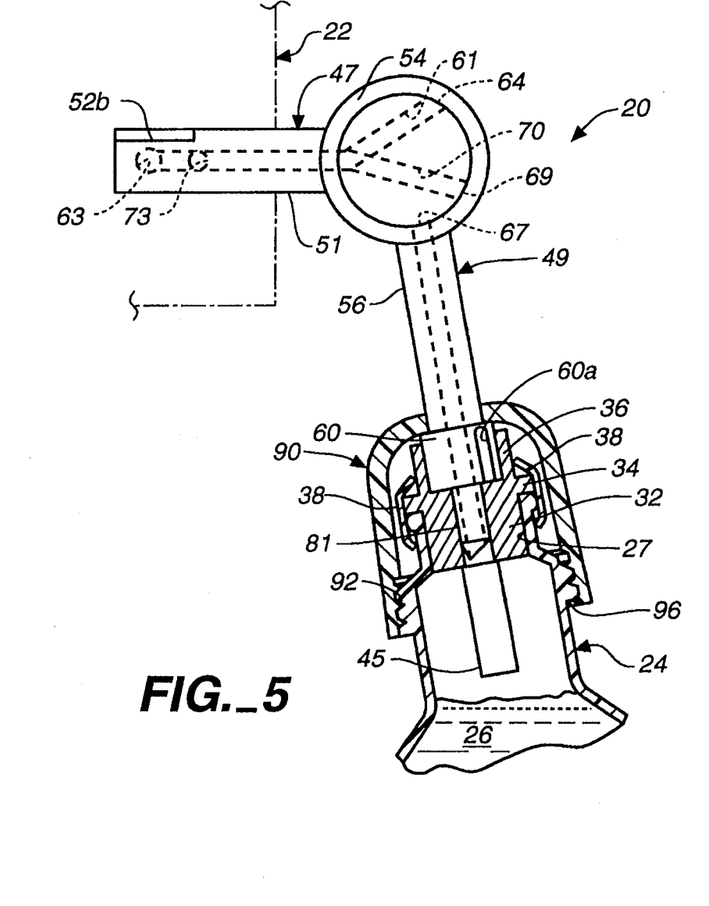
FIG. 5 is a view similar to FIG. 4 and shows the connector fully engaged with the anesthetic container.
Figure 6:
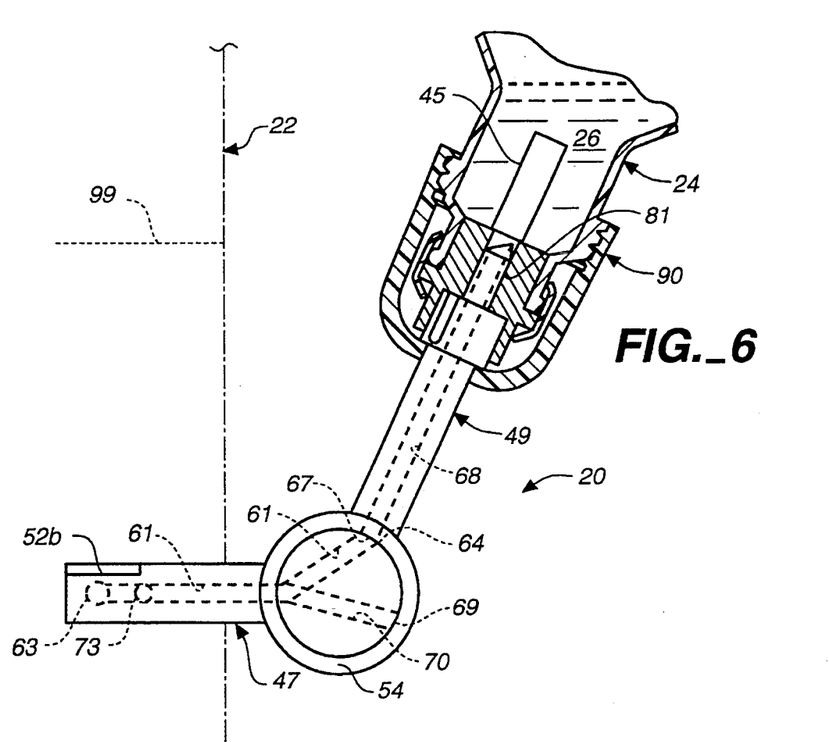
FIG. 6 is a view similar to FIG. 5, but FIG. 6 shows the second coupling moved to a raised, fill position.

A connector of the present invention is designated generally by the reference number 20 in FIG. 1 and is adapted to be mounted on one end to an anesthetic vaporizer as schematically illustrated in FIGS. 4–8 by reference numeral 22. The other end of the connector 20 is connected to a container 24 which holds liquid anesthetic 26 (FIGS. 4 and 6). The connector 20 permits draining of the inverted container 24 (FIG. 6) into the vaporizer 22 to fill the internal reservoir of the vaporizer 22.

The container 24 defines an opening or discharge port 27 (FIG. 4). In a preferred container design, the port 27 is sealed with a closure 30. The closure 30 may be molded from a resilient material (such as polyethylene) and frictionally engaged with the container 24 at the opening 27. If desired, an adhesive or sealant compound could be applied to the interior of the container 24 in the opening 27 just prior to mounting the closure 30 in the container 24.

As shown in FIG. 4, the closure 30 includes a cylindrical inner portion 32 and a larger diameter, outer flange 34. The flange 34 is adapted to seat against the end of the container 24. Preferably, a sealing sleeve, band, or ferrule 38 is applied around the end of the container 24 and the closure flange 34 to insure an effective seal. The sleeve or band 38 may be a shrink fit material that has been shrunk into tight engagement with the exterior of the container 24 and closure flange 34.

The closure 30 also includes a collar 36 projecting outwardly from the flange 34 to define a receiving socket. An inside portion of the collar 36 defines a predetermined key or shaped structure, such as a rib (not visible) for engaging a groove in the connector 20 as described in detail hereinafter.

The closure 30 provides access to the interior of the container 24 through two, parallel ports—one port 42 being visible in FIG. 4 in front of the other port 44. Port 42 functions as a discharge passage to drain the liquid anesthetic from the container 24, and port 44 functions as a vent passage for admitting gas (e.g., air) into the container 24 as the liquid contents discharge from the container through the port 42. To aid in the venting process, the closure 30 defines an inwardly projecting tube 45 which defines a continuation of the port 44.

In the initially manufactured condition, the closure 30 does not permit flow through the ports 42 and 44. To this end, the port 42 is occluded by a recessed, pierceable diaphragm or membrane 46 (FIG. 4), and the port 44 is occluded by a similar recessed, pierceable diaphragm or membrane (not visible in the Figures, but located in the port 44 at the same depth as the membrane 46).

The connector 20 has a pair of pivotably mounted couplings, a first coupling 47 and a second coupling 49 (FIG. 1). The first coupling 47 has a first leg 51 (FIG. 1) with a distal end 52 for connecting the coupling 47 to the vaporizer 22. In the embodiment illustrated, the end 52 defines a notch 52a which functions as a predetermined shape or key for mating with a corresponding or complementary structure (not illustrated) on the vaporizer 22.

The connector 20 is initially mounted to the vaporizer 22 by pushing the connector coupling 47 endwise into the vaporizer inlet port. A vaporizer designed for one type of anesthetic would have a particular configuration or key at its inlet port for mating with only one specific coupling shape of the connector 20. In this way, only a connector intended for one type of anesthetic can be connected to a vaporizer designed for that anesthetic.

The first leg 51 of the first coupling 47 has a proximal end defining a cylindrical portion 53. The cylindrical portion 53 is received in an annular wall 54 at the distal end of the second coupling 49. These parts of the two couplings function as a combination valve and mounting structure as explained in detail hereinafter.

The second coupling 49 includes a leg 56 projecting from the annular wall 54 and terminates in an enlarged boss or plug 60. The plug 60 is adapted to be received in the socket defined by the container closure collar 36 as shown in FIG. 5. A peripheral portion of the plug 60 defines a recess 60a which has a shape that is complementary to, and that is adapted to mate with, a rib (not visible) on the inside of the container closure collar 36.

Figure 3:
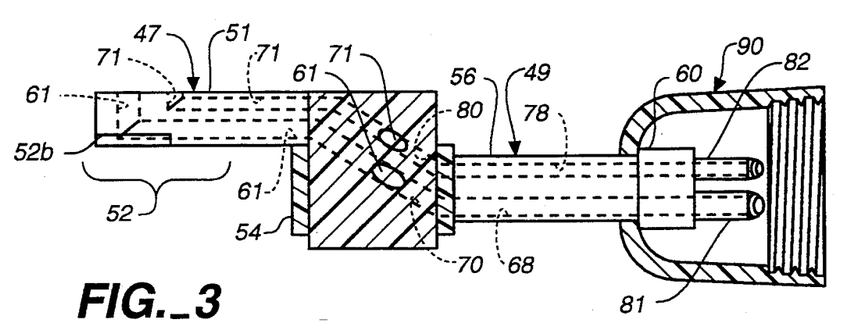
FIG. 3 is a cross-sectional view taken generally along the plane 3—3 in FIG. 2.

As shown in FIGS. 1 and 3, the first coupling 47 defines a first through passage 61. The first coupling 47 also defines a discharge port 63 at one end of the first passage 61 and defines an inlet port 64 at the other end of the first passage 61.

The second coupling 49 defines an influent port 66 and an outlet port 67 connected via a second passage 68. The first passage 61 and the second passage 68 are adapted to be selectively placed in communication by pivoting the second coupling 49 as explained hereinafter in detail.

The first coupling 47 also defines a drain port 69 and a third passage 70 which diverges from the first passage 61 and communicates with the port 69. Pivoting of the second coupling 49 to a particular position will establish communication between the third passage 70 and the second passage 68 as explained below in detail.

The first coupling 47 further defines a fourth through passage 71. A first gas vent port 73 is defined at one end of the fourth passage 71, and a second gas vent port 74 is defined at the other end of the fourth passage 71.

The second coupling 49 also defines a first gas vent port 76 and a second gas vent port 77 connected via a fifth passage 78. The fourth passage 71 and the fifth passage 78 are adapted to be placed in communication whenever the second coupling 49 is pivoted to establish communication between the first passage 61 and the second passage 68 as explained below in detail.

Finally, the first coupling 47 defines a drain vent port 79 and a sixth passage 80 which diverges from the fourth passage 71 and communicates with the port 79. When the second coupling 49 is pivoted to establish communication between the third passage 70 and the second passage 68, communication between the sixth passage 80 and the fifth passage 78 is established as explained in detail hereinafter.

As can be seen in FIGS. 1 and 3, the diverging pair of passages 71 and 80 and the diverging pair of passages 61 and 70 are angled within the cylindrical portion 53. This enables the second coupling outlet port 67 to be aligned with either the first coupling inlet port 64 or the first coupling drain port 69—depending on the rotational orientation of the second coupling 49. Similarly, the second coupling gas vent port 76 can be aligned with either the first coupling gas vent port 74 or the first coupling drain vent port 79—depending on the rotational orientation of the second coupling 49.

As illustrated in FIG. 1, the plug 60 includes a first projecting conduit 81 through which a portion of the passage 68 extends. The conduit 81 defines a hollow piercing tip at the port 66 for entering into the closure port 42 to pierce the membrane 46. The plug 60 also defines a second projecting conduit 82 through which a portion of the passage 78 extends. The conduit 82 defines a hollow piercing tip at the port 77 for entering into the closure port 44 to pierce the membrane therein (that membrane not being visible in the figures).

The plug 60 is adapted to engage the container 24 after the connector 20 has been properly connected with the vaporizer 22. First the connector second coupling 49 is pivoted to a downwardly angled, "closed" position shown in FIG. 4. In this position the second coupling gas vent port 76 and liquid outlet port 67 are occluded by the convex surface of the cylindrical portion 53 of the first coupling 47.

As illustrated in FIG. 4, the container 24 can then be located to align the socket of the closure collar 36 with the connector plug 60. The plug recess 60a is aligned with a mating closure rib (not visible) in the closure socket, and the ports 42 and 44 are aligned with the piercing conduits 81 and 82, respectively. Then, the container 24 can be pushed upwardly slightly so that the piercing conduits 81 and 82 begin to enter the ports 42 and 44, respectively, The size and shape of each conduit 81 and 82 adjacent its tip is effective to establish a liquid-tight seal around the conduit at the port as the tip begins to engage the membrane (e.g., membrane 46 in FIG. 4). The proper and complete upward displacement of the container 24 relative to the connector 20 is effected by a system which includes a collar 90 on the connector 20. The collar 90 is disposed for rotation on the connector leg 56. The inner end of the collar 90 is adapted to engage the plug 60 (FIG. 4) which has a diameter larger than the diameter of the leg 56.

The interior of the collar 90 defines a screw thread 92, and a mating screw thread 96 is provided on the container 24. Alternatively, the mating screw thread 96 could be provided on the exterior of the closure 30 outwardly of the container 24 (and the collar 90 would have to be configured as necessary to properly engage such a screw thread on the closure).

As the threaded, swivel collar 90 is engaged with the container thread 96 and tightened on the container 24, the closure ports 42 and 44 are pulled onto the plug conduits 81 and 82, respectively, and the membranes (e.g., membrane 46) are pierced (FIG. 5). The membranes are sufficiently recessed so that they are not ruptured until after a liquid-tight seal is effected between the plug conduits 81 and 82 and the mating portions of the ports 42 and 44 which are exterior of the membranes.

Typically, the closure material, at least in the region of the ports 42 and 44 exterior of the membranes, is somewhat resilient. Further, the diameters of the ports 42 and 44, exterior of the membranes, are less than the maximum exterior diameters of the conduits 81 and 82, respectively. This ensures the formation of tight seals just prior to, as well as after, the piercing of the membranes.

Preferably, the membranes are formed as unitary portions of the closure. It is presently contemplated that the preferred closure will be molded as the unitary structure from a suitable thermoplastic material (e.g., polyethylene). The pierceable membranes are preferably molded as part of the closure in the form of generally round, frangible disks or diaphragms.

After the container 24 has been properly attached to the connector 20, the connector second coupling 49 is pivoted upwardly from the closed position illustrated in FIG. 5 to a "fill" position illustrated in FIG. 6. In the fill position, the second coupling outlet port 67 is aligned with the first coupling inlet port 64. The anesthetic liquid can thus flow sequentially through the passage 68, passage 61, and out of the discharge port 63 into the vaporizer 22.

Further, when the connector 20 is in the fill position illustrated in FIG. 6 with the container 24 attached, the vent conduit 45 within the container 24 communicates with the first coupling gas vent port 73 of the first coupling 47 mounted in the vaporizer (FIG. 6). As can be seen in FIG. 1, gas can flow sequentially through the vent port 73 and fourth passage 71 to the vent passage 78 in the second coupling 49 which communicates through the inserted conduit 82 with the container vent tube 45 as shown in FIG. 5. Within the vaporizer 22 the gas vent port 73 communicates with air at atmospheric pressure to accommodate venting of air into the container 24 as the container contents 26 flow into the reservoir of the vaporizer 22.

As illustrated in FIG. 6, the reservoir of the vaporizer 22 has a nominal maximum fill elevation or level 99. Preferably, the second coupling 49 has a length sufficient to maintain the lowest part of the container 24 above the fill level elevation 99 of the vaporizer so that the container 24 can be completely emptied.

Vaporizers typically have a drain valve (not illustrated) which can be operated to open or close the inlet to the vaporizer reservoir. In the open position, it permits the vaporizer to be filled with the anesthetic liquid from the container. After the anesthetic liquid 26 has been drained from the container 24, the vaporizer valve can be closed to isolate the reservoir of anesthetic liquid in the vaporizer and prevent the liquid from draining back out through the first coupling discharge port 63. Then, the second coupling 49 can be pivoted downwardly from the "fill" position shown in FIG. 6 to a "drain" position shown in FIG. 7.

Figure 2:
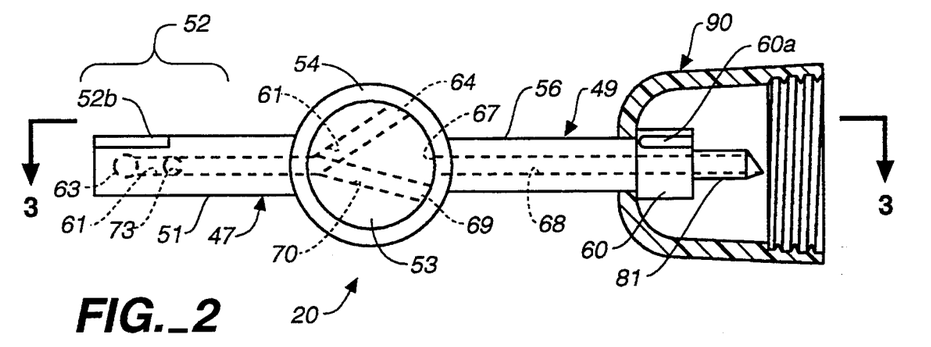
FIG. 2 is a side elevational view taken generally along the plane 2—2 in FIG. 1, but FIG. 2 shows the components assembled with a portion of one end illustrated in cross section.
Figure 7:
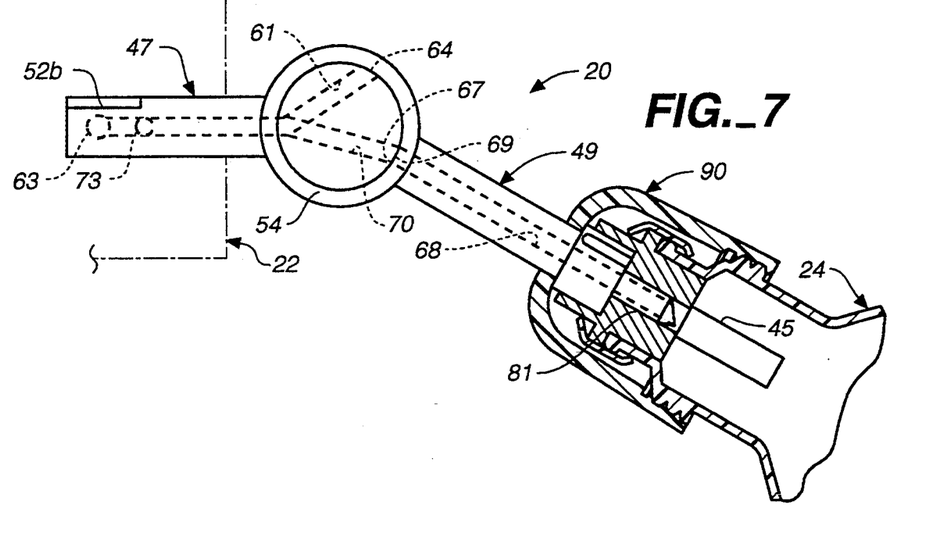
FIG. 7 is a view similar to FIG. 6, but FIG. 7 shows the second coupling moved to a lowered, drain position.

In the "drain" position, the second coupling passage 68 is in communication with the downwardly slanting passage 70 in the first coupling 47 (FIG. 7). Also, the vent passage 78 (FIGS. 1 and 2) in the second coupling 49 is in communication with the first coupling downwardly slanting passage 80 (in FIGS. 1 and 2). In the "drain" position, any residual anesthetic liquid in the connector 20 and in the upper region of the container 24 can drain to the bottom of the container 24.

In some situations when not all of the liquid anesthetic in the vaporizer has been used, it may be desirable to drain the remaining liquid anesthetic from the vaporizer reservoir. This is typically done by opening the valve on the vaporizer reservoir. In such a case, it would be especially useful to drain the vaporizer into the empty container 24 through the connector passages 61, 70, and 68. This can be accomplished by opening the vaporizer valve when the second coupling 49 is in the drain position.

Figure 8:
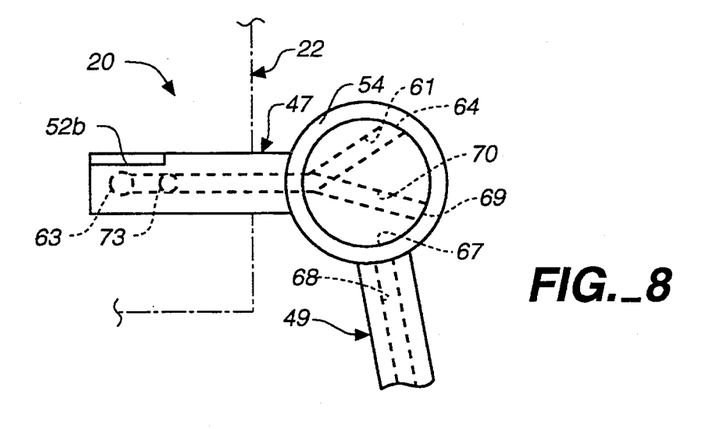
FIG. 8 is a view substantially identical to FIG. 5 and shows the second coupling in the lowered, closed position.

Next, after any anesthetic liquid has drained back into the container 24, the second coupling 49 can be rotated to the "closed" position illustrated in FIGS. 5 and 8. In the closed position, the second coupling passages 68 and 78 are occluded by the first coupling cylindrical portion 53 so no drops of liquid can leak from the first coupling 47. The container 24 can then be unscrewed from the second coupling 49 and removed from the system. The connector 20 is then ready to receive a new container 24. The empty container 24 can be removed for disposal. An auxiliary cover (not illustrated) could be installed over the end of the empty container if desired.

Although not illustrated, travel stops and/or detents can be provided in the connector 20 so that the second coupling 49 can be self-maintained in each of the three positions (the "closed" position illustrated in FIGS. 1, 5, and 8; the "fill" position illustrated in FIG. 6; and the "drain" position illustrated in FIG. 7). Further, conventional or special sealing systems, such as "O"-ring seals, lands around the ports, etc., may be employed to eliminate, control, or minimize leakage.

It will also be appreciated that the connector 20 need not be removable from the vaporizer 22. The connector 20 may be permanently attached to, or formed as an integral or unitary part of, the vaporizer 22. In some applications, such a permanent attachment is preferred.

Although the connector 20 is illustrated as having a first coupling 47 that is keyed to mate with a complementary system on the vaporizer 22, it will be appreciated that such a keying system need not be provided for those systems where the keying advantages are not desired.

Further, the type of system for connecting the connector second coupling 49 to the container 24 illustrated in the figures need not be employed exclusively. Any other suitable connection system may be used, and the details of the system for connecting the second coupling 49 to a container 24 form no part of the present invention.

It will also be appreciated that the annular wall 54 of the second coupling 49 could be interchanged with the cylindrical portion 53 of the first coupling 47. That is, the wall 54 could be a unitary part of the first coupling 47, and the cylindrical portion 53 could be a unitary part of the second coupling 49. In such a case, the orientation of the pairs of diverging passages 61/70 and 71/80 would diverge from the second coupling passages 68 and 78, respectively.

It will be readily apparent from the foregoing detailed description of the invention and from the illustrations thereof that numerous variations and modifications may be effected without departing from the true spirit and scope of the novel concepts or principles of this invention.

What is claimed:

1. A connector suitable for mounting on an anesthetic vaporizer for connecting the vaporizer with a discharge port of a container of liquid anesthetic, said connector comprising:

a first coupling attachable to said vaporizer at one end and carrying a cylindrical portion at an opposite end, and defining a first through passage communicating at said one end with said vaporizer;

a second coupling attachable to said container at one end and carrying an annular wall at an opposite end, and defining a second through passage communicating at said one end with said container discharge port;

a third passage defined by the cylindrical portion of said first coupling and permanently communicating with said first passage; and said cylindrical portion of said first coupling cooperatively received in said annular wall of said second coupling to accommodate pivoting of said second coupling to a closed position occluding said first and second passages, to a raised fill position establishing communication between said first and second passages, and to a lowered drain position in which said first and second passages communicate through said third passage.

2. The connector in accordance with claim 1 in which said first coupling defines first and second gas vent ports connected via a fourth passage;

said second coupling defines first and second gas vent ports connected via a fifth passage; and one of said couplings defines a drain vent port and a sixth passage diverging from one of said fourth and fifth passages to communicate with said drain vent port whereby, when said couplings are in said fill position, said fourth and fifth passages are in communication, when said couplings are in said drain position, said sixth passage communicates between said fourth and fifth passages, and when said couplings are in said closed position, flow between said fourth and fifth passages is occluded.

3. The connector in accordance with claim 1 in which said first coupling is attachable in fixed relation to said vaporizer.

4. A connector suitable for mounting on an anesthetic vaporizer for connecting the vaporizer with a container of liquid anesthetic, said connector comprising:

a first coupling attachable to said vaporizer and including a first leg having a distal end for insertion into said vaporizer and having a generally cylindrical portion at a proximal end of said first leg, said first leg distal end defining a discharge port and said cylindrical portion defining an inlet port, a drain port, and a third passage diverging from said first passage to said drain port;

a second coupling attachable to said container and including a second leg having a proximal end for attaching to said container and having a generally annular wall at a distal end for rotatably receiving said first coupling cylindrical portion, said second leg proximal end defining an influent port and said annular wall defining an outlet port; said influent port and said outlet port connected via a second passage; and said cylindrical portion of said first coupling being received in said annular wall of said second coupling accommodating pivoting of said second coupling relative to said first coupling among (1) a fill position in which said first and second passages are in communication through said first coupling inlet port and second coupling outlet port, (2) a drain position in which said third passage communicates between said first and second passages, and (3) a closed position occluding flow between said first and second passages.

5. The connector in accordance with claim 4 in which said first coupling cylindrical portion projects beyond an end of said annular wall.

6. The connector in accordance with claim 4 in which said first coupling and said second coupling each include a key structure making said couplings attachable only to a vaporizer and container, respectively, that each have a mating key structure.

7. The connector in accordance with claim 4 in which
said first coupling defines first and second gas vent ports connected via a fourth passage;

said second coupling defines first and second gas vent ports connected via a fifth passage; and one of said couplings defines a drain vent port and a sixth passage diverging from one of said fourth and fifth passages to communicate with said drain vent port whereby, when said couplings are in said fill position, said fourth and fifth passages are in communication, when said couplings are in said drain position, said sixth passage communicates between said fourth and fifth passages, and when said couplings are in said closed position, flow between said fourth and fifth passages is occluded.

8. The connector in accordance with claim 4 in which said second coupling includes at least one projecting conduit communicating with said second passage and defining a piercing tip engageable with a port of a container for piercing a membrane therein, the size and shape of said conduit adjacent said tip being operable to effect a liquid-tight seal around said conduit at a container port as said tip pierces a membrane; and a collar mounted for rotation on said second coupling, said collar engaging said second coupling and defining a screw thread engageable with a thread on a container and operable to pull a container port onto said conduit as increasing threaded engagement is established whereby the piercing of a membrane is effected.

9. The connector in accordance with claim 4 for use with said container in which said second coupling has a plug that includes a boss adapted for insertion into a receiving socket of a closure for a container, said socket communicating with said port; and said second coupling has a conduit which communicates with said second passage and projects from said boss for entering into said port.

10. The connector in accordance with claim 4 in which said first coupling has a generally rigid construction.

11. The connector in accordance with claim 4 in which said connector is generally Z-shaped.

12. The connector in accordance with claim 4 in which said first coupling is attachable in fixed relation to said vaporizer.

* * * * *